United States Patent [19]
Schwartz

[11] 3,994,171
[45] Nov. 30, 1976

[54] CLINICAL TESTING APPARATUS

[76] Inventor: Henry D. Schwartz, 935 Waverly St., Palo Alto, Calif. 94301

[22] Filed: Dec. 15, 1975

[21] Appl. No.: 640,542

Related U.S. Application Data

[63] Continuation-in-part of Ser. No. 320,264, Jan. 2, 1973, Pat. No. 3,941,565.

[52] U.S. Cl. .............................. 73/423 A; 23/253 R
[51] Int. Cl.² ........................................ G01N 31/00
[58] Field of Search ................... 73/423 A; 141/130; 23/253, 259, 292

[56] References Cited
UNITED STATES PATENTS

| | | | |
|---|---|---|---|
| 2,879,141 | 4/1959 | Skeggs | 73/423 A |
| 3,074,699 | 1/1963 | Skeggs et al. | 23/292 |
| 3,481,712 | 12/1969 | Bernstein | 23/292 |
| 3,627,432 | 12/1971 | Bergman | 23/292 |
| 3,684,452 | 8/1972 | Bessman | 23/253 |

*Primary Examiner*—S. Clement Swisher
*Attorney, Agent, or Firm*—Wolf, Greenfield & Sacks

[57] ABSTRACT

The testing apparatus is preferably for the measurement of ionized calcium and other ions in biologic fluids. The apparatus comprises a selectively operated turntable defined by a plurality of radially extending leaves fixed in position at one end along a circular locus, a cover overlying the turntable, and a plurality of sample cups carried by the turntable and each received by and positioned at the free end of one of the leaves. The leaves flex sufficiently to provide a bias on the cup urging the top edge of the cup into intimate contact with the bottom surface of the cover. The cover is at least partially hollow forming a plenum chamber for a saturated gas such as carbon dioxide and having a number of outlet jets spaced along a circumference of the cover with each jet for directing a flow of the gas into the cup at a suitable velocity to produce a good mixing and swirling action in the cup. In addition to the plenum mixing holes there is also an independent mixing hole at the probe station where a probe assembly comprising one or more probes is selectively and sequentially registered with the cups. The cover may also be provided with one or more sensor holes disposed outside of the mixing hole at the probe station. One sensor hole may have means associated therewith to permit introduction of an alternative gas to the cup at the probe station when this hole is blocked by a cup of special shape having a larger outside diameter. The other sensor hole may have means associated therewith to identify the cup at the probe station as containing a particular type of sample. By selection of the proper configuration of cup one can effectively program operation of the apparatus.

37 Claims, 16 Drawing Figures

CLINICAL TESTING APPARATUS

RELATED APPLICATION

This application is a continuation-in-part of applicant's copending application Ser. No. 320,264 filed Jan. 2, 1973 now U.S. Pat. No. 3,941,565 and entitled CLINICAL TESTING MEANS AND METHOD.

BACKGROUND AND SUMMARY OF THE INVENTION

The present invention relates in general to a clinical testing apparatus. More particularly, this invention pertains to a testing apparatus for making multiple sample clinical determinations of ionized calcium concentrations or other ions in body fluids.

My copending application Ser. No. 320,264 shows a testing apparatus providing these multiple samplings. Although this apparatus operates quite satisfactorily it is an object of the present invention to provide an improved clinical testing apparatus which is preferably for making multiple sample clinical determinations of original ionized calcium concentrations of body fluids.

Another object of the present invention is to provide an improved turntable type apparatus for performing a multiple sampling.

A further object of the present invention is to provide an improved cup construction for containing the fluid samples.

Still another object of the present invention is to provide a programmable cup construction operative in conjunction with sensor means to control operation at the probe station such as by controlling the introduction of an alternative gas at the probe station.

The preferred testing apparatus is for making multiple sample clinical determinations of original ionized calcium concentrations of body fluids taken from a body. This apparatus comprises a rotatable turntable for removably carrying a plurality of body fluid sample containers or cups preferably having upwardly facing container mouths. The rotatable turntable is defined by a plurality of radially extending leaves supported in a cantilever fashion and thus fixed in position at one end along a circular locus. A cover is positioned over the turntable to substantially close the container mouths while permitting rotational movement of the turntable with respect to the cover. Means are providing for rotating the turntable with respect to the cover at predetermined time intervals to advance each of the containers to successive stations and eventually to the probe station. Each leave flexes downwardly thus permitting the cup to be inserted on the leaves and in intimate contact with the bottom surface of the cover. In the disclosed embodiment the leave has at its free end an erect post of partially spherical shape that engages with a frusto-conic cavity in the base of the cup or container The gas means including a plenum chamber in the cover pass a gas such as a water saturated carbon dioxide gas to each of the cups at predetermined stations about the cover. The cover has associated therewith a probe assembly comprising one or more probes which are selectively and sequentially registered with the cups.

In accordance with the present invention the cups may be constructed in different sizes or top configurations with the size of the cups functioning to program one or more operations of the apparatus. For example, when a regular cup is used the outlet jets from the cover pass the gas into the cup at a suitable velocity to produce a mixing action of the fluid in the cup. Alternatively, if a cup with a smaller inside diameter is selected the mixing hole is then blocked thereby preventing mixing of the contents in the cup. In still another embodiment also having a smaller inner diameter the cup may be provided at its mouth with an annular channel or tunnel communicating with the mixing hole and including a vent in the cup from the tunnel for venting the gas or an additional hole in the cover for coupling this positive pressure to a signalling device or permitting the introduction of an alternative gas, for example, into the cup at the probe station.

In still another embodiment there may be provided one or more additional holes which are sensor holes and are positioned to be at all times external to the internal diameter of any cup that may be used. These holes do not permit gas transit for the purpose of mixing but rather are for the purpose of sensing. The purpose of the first sensor hole is to permit introduction of an alternate gas, different from the gas in the plenum chamber of the cover to the probe station cup. When a normal cup is used the alternative gas is vented through this sensor hole. However, when the hole is blocked by means of a cup with a wide mouthed flange the gas seeks an alternative route which may be provided for by a flexible conduit leading to a mixing hole mounted within the confines of the probe holder, thus introducing this alternate gas into the cup disposed at the probe station. The second sensor hole may be disposed radially outside of the first sensor hole and may be used to provide a signal which can be used for many different purposes but is commonly used to identify the fact that the cup contains a standard to be used for automatic electrode calibration. This indication is achieved in a similar manner to that discussed with reference to the first sensor except that the alternative route may lead to a pressure switch for generating a desired electrical signal.

In accordance with another aspect of this invention there is provided a heating means in association with the cover and associated plenum chamber. The gas which hits the sample liquid in the cup is required to be both at the same temperature as the sample itself and also fully saturated with water vapor at that temperature. The heating means provides heat which is conducted and radiated to the cups and sample. The plenum chamber is preferably heated slightly above the temperature of the saturated entering gas which temperature is the same as the intended temperature of the sample at the time of measurement. It has also been found that having the plenum temperature slightly raised prevents condensation in the plenum of the cover. When the gas is then exited through the jets from the plenum chamber the decrease in pressure causes a decrease in temperature to the desired temperature and at the same time the gas is again fully saturated as its exits at essentially atmospheric pressure into the cup.

BRIEF DESCRIPTION OF THE DRAWINGS

Numerous other objects, features and advantages of the invention should now become apparent upon the reading of the following detailed description taken in conjunction with the accompanying drawings, in which.

DETAILED DESCRIPTION

Figure 1:
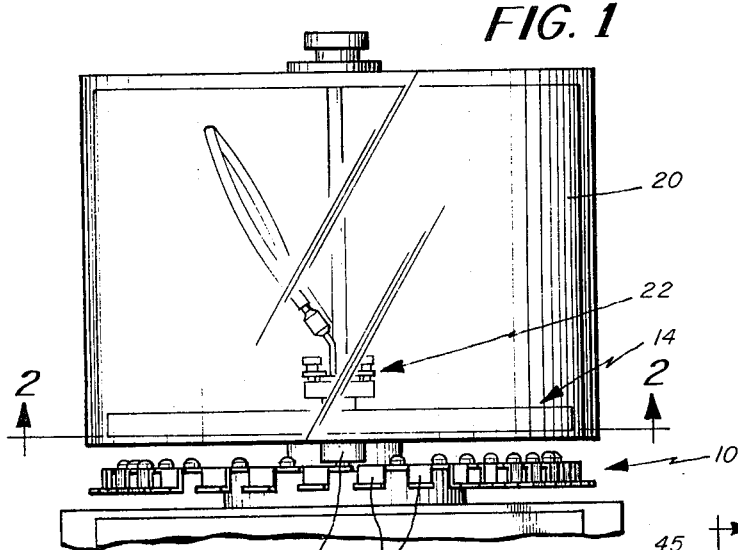
FIG. 1 is a front view of the apparatus of this invention showing in particular the turntable, cover and probe assembly.
Figure 2:
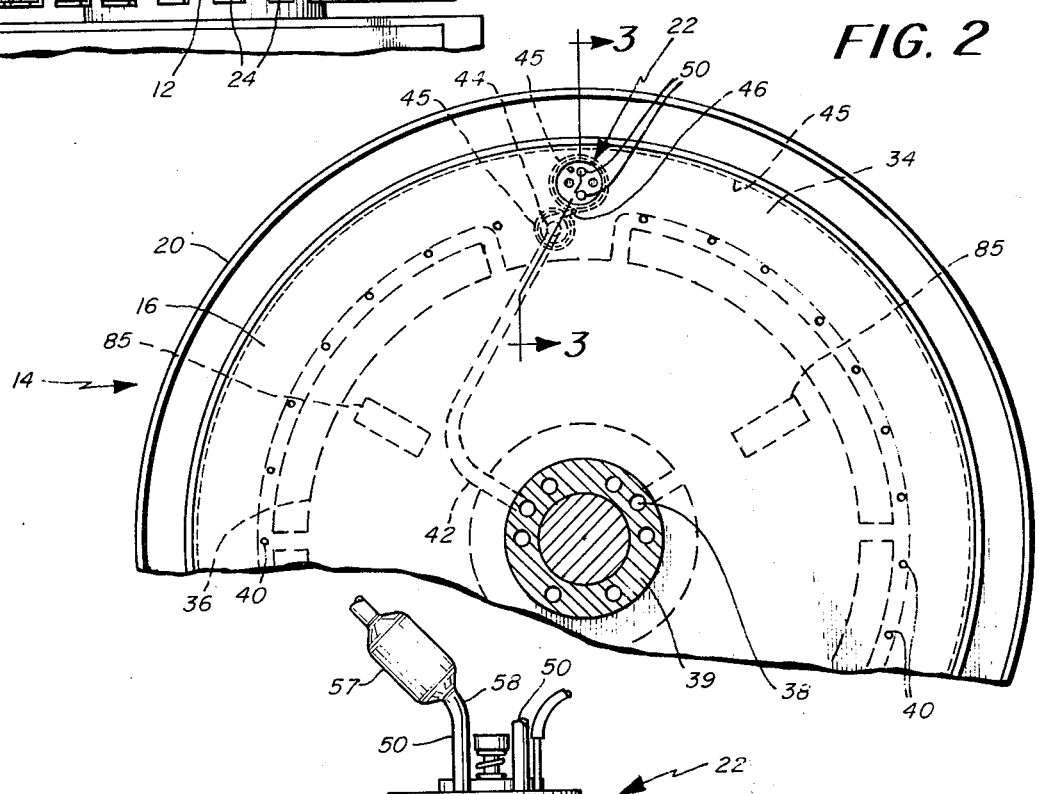
FIG. 2 is a fragmentary cross-sectional view partially cut away and taken along line 2—2 of FIG. 1.
Figure 3:
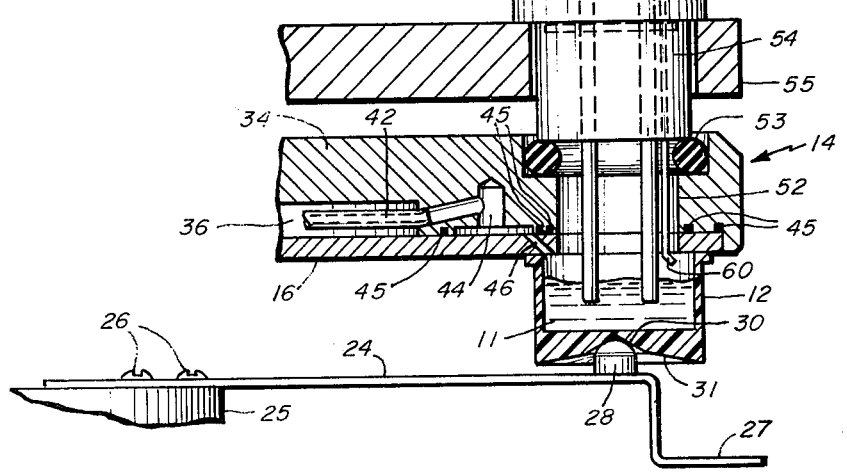
FIG. 3 is a cross-sectional view taken along line 3—3 of FIG. 2.

Referring now to the drawings and in particular to FIGS. 1–3, the testing apparatus comprises a rotatable turntable 10 which may hold 30 cups 12 and rotates with respect to the cover 14. As the turntable rotates the cups slide smoothly with their mouths urged in intimate contact against the stainless steel plate 16 comprising a part of the cover 14.

The system shown in FIG. 1 including the turntable, cover, and electrostatic shield 20 is suspended about a central axis up through which all linkage elements run thus providing complete axis peripherally to all of the cup positions without interference from overhanging hardware. The linkage elements may comprise a linkage for operating the probe assembly 22 so that this probe assembly is lifted to its upper position withdrawing the probes out of the cups preparatory to rotation of the turntable.

The cover is maintained in a fixed position and there is also provided a rotating mechanism such as a Geneva drive system for selectively driving the turntable.

The turntable 10 comprises a plurality of radially arranged cantilever leaves 24 suitably supported at one end to the hub 25 by means of bolts 26, for example. The hub 25 is selectively rotated as hereinbefore mentioned. At their free end and each leave has a tab 27 which may be depressed to permit insertion of the cup 12 onto the leaf so that it is as seated in FIG. 3. The leave 24 has affixed thereto a post 28 preferably having a spherical shape top for mating with a frustoconic cavity 30 in the base wall 31 of the cup 12 as shown in FIG. 3. The support arrangement including post 28 in FIG. 3 provides a simple means for supporting the cup with a slight bias being provided by the leave 24 urging the cup into intimate contact with the bottom surface of the stainless steel plate 16.

In addition to the plate 16, the cover 14 comprises a solid disc 34 defining a hollow plenum chamber 36. The gas which may be a carbon dioxide gas is introduced into the plenum chamber 36 through a port 38. The carbon dioxide gas or oxygen or other gas is preferably bubbled through warmed water and delivered moist to the system. A pressure regulator is used which is capable of maintaining a constant pressure in the plenum 36 which pressure is independent of flow rate and which thereby provides jets of the gas through the mixing holes 46 as shown in FIG. 2 to produce good mixing and swirling action in the cup. FIG. 3 shows the cup at the probe station whereas the other mixing holes 46 shown in FIG. 2 are for mixing at positions other than the probe station position. In my copending application Ser. No. 320,264 the angular displacement of the mixing holes is shown to provide the desired mixing and swirling action in the cup.

FIGS. 2 and 3 show the probe assembly 22 which is, of course, disposed at the probe station for sampling the fluid 11 disposed in the cup 12. A gas which is possibly different from the gas in the plenum chamber 36 may be introduced via a conduit 42 to a small chamber 44 and from there by way of a diagonal port 46 to the inside of the cup. For sealing purposes there may be provided a plurality of O-rings 45 as shown in FIGS. 2 and 3.

The probe assembly comprises a plurality of probes 50 which extend into the fluid 11 for sampling the fluid at the probe station. The bottom ends of the probes extend through an opening 52 in the cover. Each of the probes is supported in a cylindrical support structure 54. This support structure may rest upon an O-ring 53 as shown in FIG. 3. The support structure 54 is shown in its lower position and is supported by a carrying member 55. The probe assembly lifts when the member 55 is lifted. The lifting of the probe assembly is timed with the rotation of the turntable so that the turntable cannot rotate unless the probe assembly has been lifted to its upper position.

With the arrangement of the present invention it may be desirable to use a number of different probes supported in the holder 54. Each of the probes includes an enlarge chamber 57 and is bent at an angle at point 58 as shown in FIG. 3. With this bend it is easier to accommodate a greater number of the probes in the holder 54. The probes, as shown in FIG. 1, have an electrical connection in the form of a coaxial lead which may extend down through the member 39 (see FIG. 2), for example, to an electronic system in the device.

With reference to FIGS. 2 and 3 it is noted that there is essentially a separate gas line coupled to the chamber 44 at the probe station. It has been found that it is sometimes desirable to be able deliver to the sample being measured at the probe station a gas which is different from that which all of the other cups in the main plenum stations are receiving, or sometimes deliver gas only to the cup at the probe station and not to the other cups. For example, one might wish to measure for a prolonged period one sample at the probe station and avoid wasting gas by delivering it to 29 other positions which do not have cups. Alternatively, one might wish for example to deliver oxygen or some special gas to the cup at the measuring station and deliver a different gas or no gas to the other cups. For example, if it is desired to measure an aqueous, protein-free solution at the probe station, such a solution measuring more stable when it receives oxygen or some inert gas but not being able to tolerate carbon dioxide gas, while at the same time mixing cups at the other station may contain blood serum with carbon dioxide of a desired composition. It has been found that readings with specific ion electrodes in any solution are more stable and more crisp, with better electrode response and slopes, if those solutions are being actively mixed during the measurement. It is desirable for the most part that blood serum samples, which contain proteins, be mixed with a gas which contains carbon dioxide of such partial pressure that it will produce a pH in a particular range. When mixing aqueous, protein-free solutions carbon dioxide gas cannot be tolerated, since in the absence of the buffering effect of any protein the pH of such aqueous solutions is rendered extremely acidic, such as below 5.0 or 4.5, a range in which current calcium electrodes measure hydrogen ion as well as calcium ion activity. Therefore, it is desirable that such aqueous solutions be mixed with a relatively inert gas such as nitrogen or oxygen to displace and thereby drive off carbon dioxide which has become dissolved in said aqueous solution as commonly occurs. The apparatus described herein permits this to occur wherein the gas jet which serves the cup being measured at the probe station is circumscribed and kept separate from the rest of the plenum area. By means of a simple selector valve arrangement may be provided external to the chassis to the machine where the various gas inputs are derived, the same gas which goes to the plenum could also be directed to the probe station if desired.

It is sometimes desirable that certain predetermined cups containing specified solutions receive, when they are at the probe station, a gas which is different from that in the plenum and which is also different from the gas which other non-specified cups receive when they are at the probe station. To provide for this alternative gas there may be provided a thin piece of tubing 60 shown in FIG. 3 and extending down the probe assembly 22 terminating in the cup 12. This tubing 60 may be bent at its bottom end to provide efficient mixing in the cup in a similar manner to the action provided by the mixing jets 40 in the plate 16. The top free end of the tubing 60 may be connected to a flexible tube to an external gas supply. The programming of this alternative gas supply is discussed in more detail hereinafter.

The system of the present invention is intended to be quite versatile and to meet the need of a variety of applications to permit use of specific ion electrodes in both biological, protein-containing fluids and in non-biological, non-protein-containing fluids. Thus, in accordance with the invention it is desirable to be able to provide that a particular sample will either be mixed with the gas or will not be mixed, and that if it is mixed, there is a choice of two types of gases with which it can be mixed. Furthermore, it is desirable that certain cups be identified as being standards for subsequent use in calculating the value of unknown samples run in proximity to the standards. However, it is awkward if it becomes necessary to program into the machines special information as to what cup is in what particular side of the machine in advance. Therefore, in accordance with the invention it has been found that it is desirable to have some means by which one places a sample in a certain type of cup which is so configured as to permit or prevent the entry of gas. The mechanism by which this is accomplished is by varying the diameter of the cup. The size of the cup is essentially programmed to effect certain sequences of operation as will be discussed in more detail hereinafter.

Figure 4:
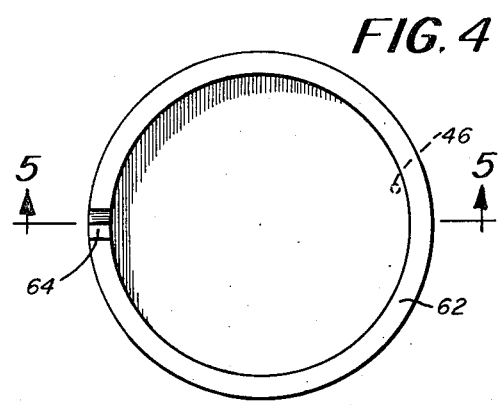
FIG. 4 is a plan view of a first embodiment of a cup constructed in accordance with this invention.
Figure 5:
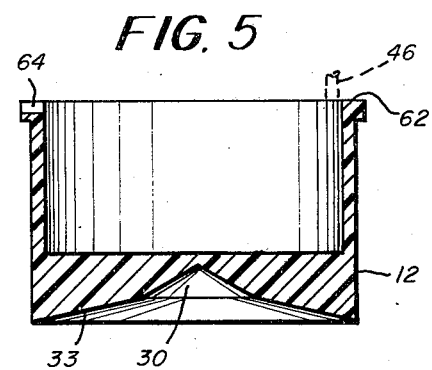
FIG. 5 is a cross-sectional view of the cup shown in FIG. 4.

FIGS. 4 and 5 show the most basic cup construction. As previously mentioned this cup has a frustoconic cavity 30 contiguous with a slightly tapered bottom wall 33. This cup may have an internal diameter of approximately 1 inch in a depth from the mouth 62 of the cup to the bottom inner surface of approximately ½ inch. In FIG. 4 there is shown in dotted the outline of the overlying mixing hole 46 which is just slightly inside of the inner diameter of the cup 12 thus permitting mixing in the cup. The cup also has a notch 62 or alternatively a hole near the top of the cup to permit gas to escape to prevent a back pressure. In this way the gas from the mixing jet of hole 40 can freely enter the cup and mix the contents thereof.

Figure 6:
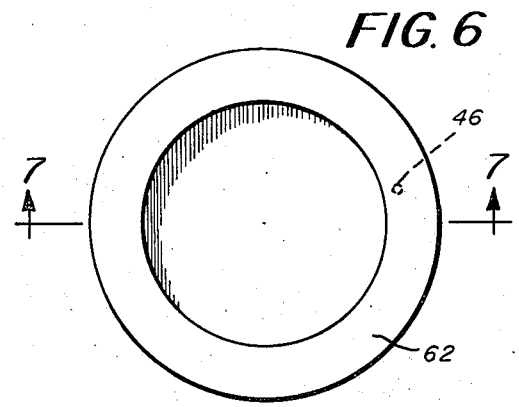
FIG. 6 is a plan view of another embodiment of a cup.
Figure 7:
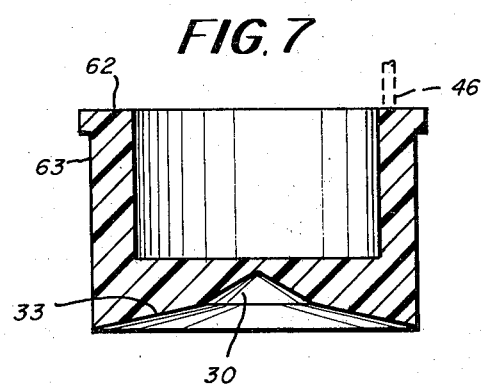
FIG. 7 is a cross-sectional view taken along line 7—7 of FIG. 6.

FIGS. 6 and 7 show an alternative arrangement for the cup which is referred to as a no-mix cup. The cup shown in FIGS. 6 and 7 is of quite similar construction especially as far as the bottom area of the cup is concerned. However, this cup has a thicker wall 63 with a reduced inner diameter that may be on the order of 0.8 inches. There is no notch or hole provided in the mouth 62 and furthermore, it is noted in FIG. 6 that the representation of the mixing hole 46 lies outside of the inner diameter of the cup. Thus, the mouth of the cup essentially blocks the mixing action which may be desirable under some circumstances.

Figure 8:
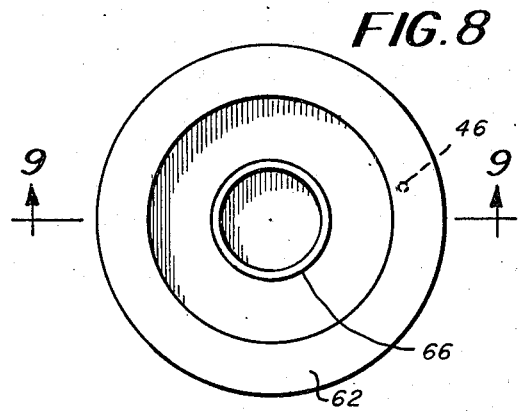
FIG. 8 is a plan view of still another embodiment of a cup having a partitioning wall inside thereof.
Figure 9:
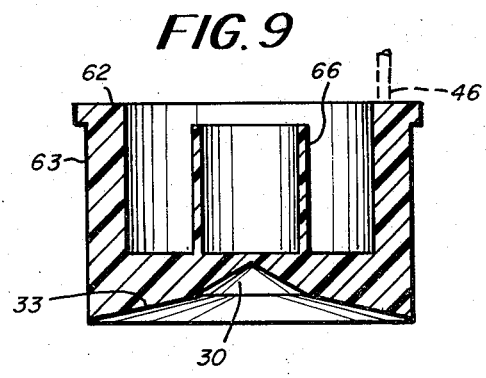
FIG. 9 is a cross-sectional view taken along line 9—9 of FIG. 8.

For some no-mix application it may be desirable to use a cup construction as shown in FIGS. 8 and 9. This is used where two different materials are to be contained in the cup. The pH and reference system should be stored wet whereas some calcium electrodes and some other specific ion electrodes are to be stored dry. In addition, the solutions necessary to standardize the pH electrodes are often very harmful to calcium and other specific ion electrodes. It is therefore desirable to have a convenient way to calibrate the pH electrode with its solution without bringing the other electrodes into contact with the pH electrode. Further it is convenient to store the pH and reference electrodes wet while the others are stored dry. Thus, the arrangement shown in FIGS. 8 and 9 using a special cup providing a separate well or chamber which can accommodate one or more electrodes is desirable. Typically the pH in reference electrode would fit within the well.

The cup construction of FIGS. 8 and 9 is substantially identical to the construction shown in FIGS. 6 and 7 but adds a centrally disposed tube 66 which partitions the cup into two separate concentric areas. As previously mentioned there may be provided more than one probe 50 in the probe assembly 22. In a preferred arrangement there is a center probe in a plurality of peripherally arranged probes. Thus, the centrally disposed probe may be for sampling a first liquid inside of the tube 66 and one of the peripheral probes may be used for sampling a different fluid in the space between the tube 66 and the wall 63 of the cup.

Figure 10:
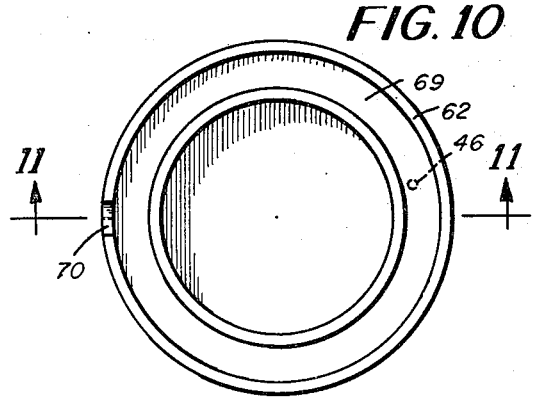
FIG. 10 is a plan view of still another cup structure.
Figure 11:
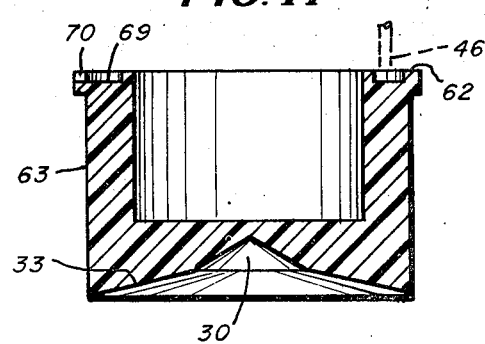
FIG. 11 is a cross-sectional view taken along line 11—11 of FIG. 10.

FIGS. 10 and 11 show still another construction of a cup in accordance with the present invention. This cup construction may be used as a no-mix cup. It is noted that the mixing hole 40 communicates with a channel 69 and there is provided a notch 70 for exiting the gas from the channel 69. Alternatively, there may be no notch for venting but rather a hole may be provided in the cover which opens above the channel 69. This hole may couple to a pressure sensing device for generating a signal. For example, this signal could be used to enable the alternate gas line 60 shown in FIG. 3 to permit an alternate gas to enter the cup but only at the probe station.

Figure 12:
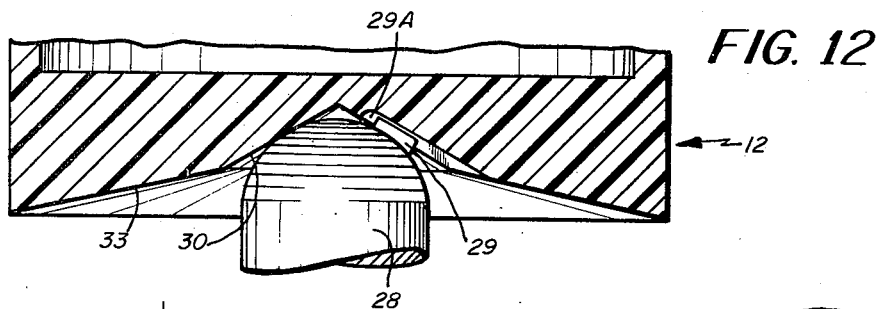
FIG. 12 is a fragmentary cross-sectional view of a slightly different embodiment of the cup and cup support shown in FIG. 3 which prevents rotation of the cup relative to its support.

FIG. 12 is a fragmentary view of a cup which may be the cup construction shown in FIG. 9. Actually, in accordance with this invention the cup may be partitioned in many different manners and in that case it is desirable to fix the cup in position relative to the support posts 28 so that the cup does not rotate relative thereto. Thus, in FIG. 12 the post 28 is shown as having a key 29 fitting within a keyway 29A. This arrangement prevents rotation of the cup 12 relative to the support post 28.

In FIG. 3 the cup is shown having a cavity in its bottom wall for receiving post 28. In an alternate arrangement in accordance with the invention the post 28 or even the leaf 24 itself may have a concavity therein. In that case the base of the cup has a nipple or post for fitting in the concavity thus supporting the cup in a slightly different manner.

In connection with the supporting of the cup it is noted that this particular support arrangement shown in FIG. 3 provides for accurate radial positioning of the cup and permits the application of an upward force by the tension provided by the lead 24 which upward force is sufficient to provide intimate contact between the top of the cup and the cover. This contact is maintained even as the cup rotates relative to the cover. Although this contact permits rotational movement there may still be provided a full hermetic seal by means of the proper selection of materials for the plate 16 and the cup.

Figure 13:
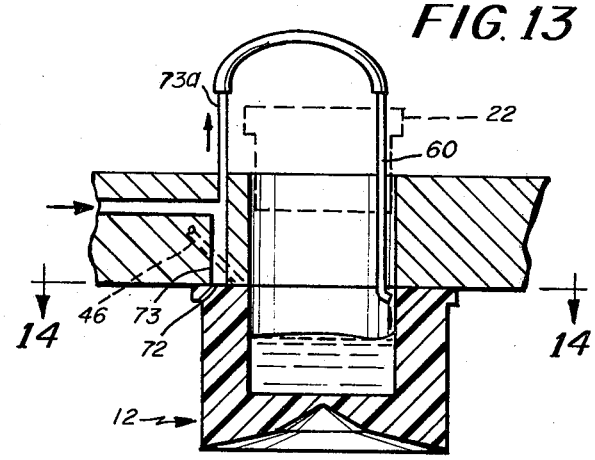
FIG. 13 is a cross-sectional view through another embodiment of the cup and also showing means for introducing an alternative gas into the cup.
Figure 14:
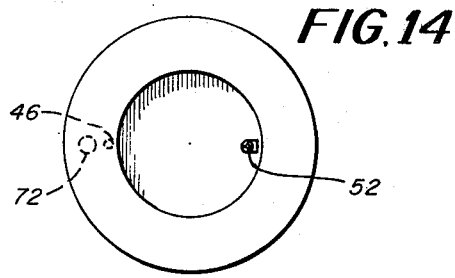
FIG. 14 is a cross-sectional view along line 14—14 of FIG. 13.

At the probe station there are preferably provided two additional holes, positioned to be external to the internal diameter of any cup that is used. These holes therefore do not permit gas flow into the cup for purposes of mixing but rather may be defined as sensor holes. The purpose of the first sensor hole is to permit introduction of an alternative gas different from the gas in the plenum chamber to the cup at the probe station. When a normal cup is in place the sensor hole is vented. However, when this hole 72 is blocked as shown in FIGS. 13 and 14 the alternative gas seeks an alternate route via conduit 73 to a mixing hole mounted within the confines of the probe holder. FIG. 13 shows this in a schematic fashion with the conduit 60 extending down into the cup 12 at the probe station. Obviously, in order to block the sensor hole 72 the cup external diameter must be larger than that used with the regular cup. If a regular cup were at the probe station then the hole 72 is vented and the hole 46 is a mixing hole. In FIG. 13 it is noted that the conduit 73 leading to the hole 72 is of a larger size than the conduit 73A. Thus, when a regular cup is used the alternative gas is vented rather than flowing in the conduit 73A.

Figure 15:
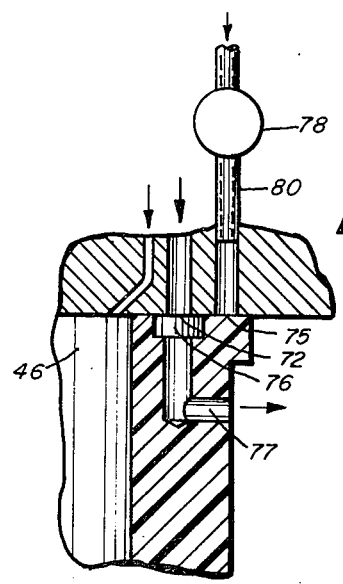
FIG. 15 is a cross-sectional view of still another arrangement in accordance with the present invention.

As previously mentioned there may also be provided a second sensor hole shown by reference character 75 in FIG. 15. FIG. 15 is a fragmentary view of a cup at the probe station and showing the mixing hole 46, the first sensor hole 72 and the second sensor hole 75. In this particular embodiment the cup is of the type including a channel 76 and an output vent 77. The purpose of the sensor hole 75 is to provide a signal which can be used for many different purposes but which is preferably used to identify the fact that the particular cup contains a standard to be used for automatic electrode calibration. It is noted in FIG. 15 that this port is blocked. A flow meter 78 may be provided in the conduit 80 leading to the sensor hole 75. If this hole is blocked the flow meter 78 may provide an electrical signal which controls certain operations in the apparatus. It is noted in the embodiment of FIG. 15 that the hole 46 is unblocked and thus mixing occurs in the cup but a special signal is provided by way of an output from the flow meter 78 indicating that a standard is being tested.

In still a further embodiment of the invention similar to that shown in FIG. 15 the mixing hole 46 may also be blocked by a cup of smaller internal diameter. In that case the pressure applied through the conduit 77 may be used to operate a valve for permitting the alternative gas to pass to the cup such as by way of the tube 60 shown in FIG. 3.

It has been found that the pH of a blood sample is quite significantly dependent upon temperature. It is therefore desirable to maintain a steady temperature. In accordance with the present invention heating elements 85 may be used as shown in FIG. 2 and are embedded in the cover. These heating coils may connect to a temperature regulating system for maintaining the temperature of the cover at a predetermined temperature. It has also been found that this heating eliminates any condensation on the cover that may occur because of the passage of the saturated gas through the plenum chamber. It has been found that if the incoming gas is maintained at say 37° C., the cover tends to maintain that temperature of the sample at 37° C. even though the cover is at say 39° C. Having the cover at the elevated temperature reduces the saturation of the layer of gas in contact with the cover thereby eliminating condensation on the cover. When the gas then passes through the relatively small jet and undergoes a pressure drop this insures that the temperature of the gas entering the cup is at or close to the desired temperture of 37° C. This also insures that the gas at 37° C. is fully saturated with water vapor as it was when it first entered the plenum.

Figure 16:
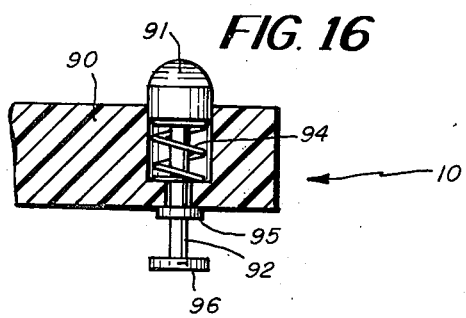
FIG. 16 shows an alternative support for the cup.

FIG. 16 shows a slightly different embodiment for the turntable 10 which uses a solid disc 90 in place of the flexible leaves 24. The spring action in accordance with this invention is provided by a deflecting mechanism including a post 91 carried by an elongated rod 92. The disc 90 is provided with a hole for receiving the post 91 and has a spring 94 disposed within the hole tending to urge the post 91 upwardly. A stop 95 is provided which may be adjustable for limiting the upward position of the post 91. At the bottom of the rod 92 there is a finger grip 96 which may be used for pulling the post 91 downwardly when a cup is to be inserted on the turntable.

What is claimed is:
1. A testing apparatus for measuring ions in body fluids comprising,
   a rotatable turntable having a plurality of radially extending leaves each having a fixed end and a free end,
   a plurality of sample containers each having an upwardly facing container mouth,
   means on the free end of each leaf for supporting the base of the container,
   a cover positioned over said turntable to close said container mouths while permitting rotational movement with respect to said cover, means for selectively rotating said turntable with respect to said cover to advance each of said containers to successive stations,
and gas carrying means carried by the cover having plural gas outlet means for passing a gas to the containers.

2. A testing apparatus as set forth in claim 1 wherein each leaf is cantilever supported having a distance from the container support means to the bottom of the cover that is less than the height of the container so that a biasing force is provided urging the cups into intimate contact with the cover.

3. A testing apparatus as set forth in claim 1 further comprising at least one sampling probe at one of said stations for sampling fluid in the container at said one station.

4. A testing apparatus as set forth in claim 3 wherein the sampling probe comprises a tube having an enlarged area and a bend therein.

5. A testing apparatus as set forth in claim 1 wherein said leaves each have tab means permitting one to flex the leaf for loading the cup.

6. A testing apparatus as set forth in claim 1 wherein said means for supporting includes a post extending upwardly from the leaf.

7. A testing apparatus as set forth in claim 6 wherein the post has a spherical top and said container has a frustoconic cavity in its base for engagement with the post.

8. A testing apparatus as set forth in claim 1 including an electrostatic shield disposed over the cover and turntable.

9. A testing apparatus as set forth in claim 3 including a plurality of sampling probes and means for commonly supporting all the probes.

10. A testing apparatus as set forth in claim 3 wherein said gas carrying means comprises a plenum chamber having the gas outlet passages terminating in mixing holes in the bottom surface of the cover.

11. A testing apparatus as set forth in claim 10 wherein said one station further mounts an independent gas input means independent of said carrying means terminating in a probe station mixing hole.

12. A testing apparatus as set forth in claim 1 including heating means disposed in the cover.

13. A testing apparatus as set forth in claim 11 including means defining a sensing port in the cover disposed outside of the probe station mixing hole and means including gas conduit means coupled from the sensing port for detecting a blockage of the sensing port by a container of predetermined size.

14. A testing apparatus as set forth in claim 13 including means defining a second sensing port in the cover disposed outside of the first sensing port and means for coupling gas independently to both first and second ports.

15. A testing apparatus as set forth in claim 1 wherein said container has an internal diameter dimensioned to block mixing holes.

16. A testing apparatus as set forth in claim 1 wherein said container has a wide mouth with an annular channel communciating with the mixing hole.

17. A testing apparatus as set forth in claim 1 wherein said container has at least one partitioning wall therein.

18. A testing apparatus as set forth in claim 17 wherein the partitioning wall is in the form of a tube dividing the container into two concentric fluid holding chambers.

19. In a testing apparatus for measuring ions in body fluid which apparatus comprises a rotatable turntable with a plurality of containers mounted thereon, and a cover overlying the turntable and contacting the container mouths, the improvement comprising, heating means at least partially in the cover for maintaining a gas passing through the cover at a predetermined temperature.

20. A container for a body fluid comprising a cup open at the top defining a cup mouth and having a base with a cavity therein from which the cup is supported.

21. A container as set forth in claim 20 wherein said cavity has a frustoconic shape.

22. A container as set forth in claim 20 including a partitioning wall within the cup dividing the cup into separate compartments.

23. A testing apparatus as set forth in claim 1 including means for preventing relative rotational movement between the container and supporting means for the container.

24. A testing apparatus as set forth in claim 7 wherein said post and cavity have keying means associated therewith preventing the container from rotating relative to the post.

25. In a testing apparatus for measuring ions in body fluid which apparatus comprises a rotatable turntable with a plurality of containers mounted thereon, a cover overlying the turntable and contacting the container mouths, means for selectively rotating the turntable to successive stations, probe means at one of said stations for sampling fluid in the container, and gas carrying means carried by the cover having plural gas outlet means for passing a gas to the containers and including an independent gas conduit defining a probe station mixing hole, the improvement comprising, means defining a sensing port in the cover disposed outside of the probe station mixing hole and means for passing a gas through the sensing port which may be blocked by a cup of predetermined size.

26. In a testing apparatus as set forth in claim 25 in combination with a cup of maximum internal radius smaller than the radius to the sensor port whereby the gas from the sensor port does not enter the container.

27. In a testing apparatus as set forth in claim 26 wherein said cup has an outer diameter at least at its mouth that blocks the sensor port.

28. In a testing apparatus as set forth in claim 25 including a second sensing port in the cover disposed outside of the first sensor port and means for passing a gas through the second sensing port.

29. In a testing apparatus as set forth in claim 28 in combination with a cup having an outer diameter at least at its mouth that blocks the second sensing port.

30. In a testing apparatus as set forth in claim 29 wherein said cup has an annular channel communicating with the first sensing port.

31. In a testing apparatus as set forth in claim 27 including an alternative gas line that conveys gas to the container when the first sensing port is blocked.

32. In a testing apparatus as set forth in claim 29 including a flow detecting means coupling to the second sensing port.

33. A container as set forth in claim 20 wherein said cup has means defining a vent to permit the escape of gas from the cup.

34. A container as set forth in claim 20 in combination with a cover overlying the cup, said cover having a mixing hole and said cup having an inner diameter that blocks the mixing hole.

35. A container as set forth in claim 20 in combination with a cover overlying the cup said cover having a mixing hole and said cup having a channel communicating with the mixing hole.

36. A container as set forth in claim 33 wherein said vent comprises a notch in the wall of the cup at its mouth.

37. A testing apparatus for measuring ions in body fluids comprising, a turntable, a plurality of sample containers each having an upwardly facing container mouth, a cover positioned over said turntable to close said container mouths, said turntable having means for biasing the cups against the cover, means for selectively rotating the turntable, and gas means carried by the cover including plural gas outlets for passing gas to the containers.

* * * * *